United States Patent [19]

Baier et al.

[11] Patent Number: 4,803,171
[45] Date of Patent: Feb. 7, 1989

[54] REAGENT PAPER FOR IMMUNOLOGICALLY ANALYSIS, A PROCESS FOR THE PREPARATION THEREOF AND THE USE THEREOF

[75] Inventors: Manfred Baier, Seeshaupt; Klaus P. Kaspar, Asuncion; Rainer Schäfer, Seeshaupt; Ulrich Träger, Limburgerhof; Siegfried Nötzel, Wilhelmsfeld, all of Fed. Rep. of Germany

[73] Assignee: Boehringer Mannheim GmbH, Mannheim-Waldhof, Fed. Rep. of Germany

[21] Appl. No.: 940,500

[22] Filed: Dec. 11, 1986

[30] Foreign Application Priority Data

Dec. 11, 1985 [DE] Fed. Rep. of Germany ....... 3543749

[51] Int. Cl.[4] ..................... G01N 33/52; G01N 33/53; G01N 33/543; G01N 33/545
[52] U.S. Cl. ....................................... 436/530; 422/56; 435/805; 436/531; 436/810
[58] Field of Search ....................... 436/530, 531, 810; 435/805; 422/56

[56] References Cited

U.S. PATENT DOCUMENTS 4,366,241 12/1982 Tom ................................. 436/541 X
4,444,880 4/1984 Tom ................................. 436/810 X

FOREIGN PATENT DOCUMENTS 0082345 6/1983 European Pat. Off. .
0097952 1/1984 European Pat. Off. .
0162302 11/1985 European Pat. Off. .
1369139 10/1974 United Kingdom .

*Primary Examiner*—Sidney Marantz
*Attorney, Agent, or Firm*—Felfe & Lynch

[57] ABSTRACT

The present invention provides a process for the preparation of a reagent paper for immunological analysis, wherein a fiber fleece of a cellulose/synthetic fiber mixture, in which the weight ratio of cellulose/synthetic fiber is 1 to 90/99 to 10, is activated by treatment with periodate, the so activated fiber fleece is loaded with an acid-treated protein and non-bound protein is removed.

The present invention also provides a reagent paper for immunological analysis, wherein it comprises a fiber fleece of a cellulose/synthetic fiber mixture, in which the weight ratio of cellulose/synthetic fiber is from 1 to 90/99 to 10.

Furthermore, the present invention is concerned with the use of a fiber fleece of a cellulose/synthetic fiber mixture, wherein the weight ratio of cellulose/synthetic fiber is 90 to 1/10 to 99, as reagent carrier for heterogeneous immunological analysis.

36 Claims, No Drawings

REAGENT PAPER FOR IMMUNOLOGICALLY ANALYSIS, A PROCESS FOR THE PREPARATION THEREOF AND THE USE THEREOF

The present invention is concerned with a reagent paper for immunological analysis, with a process for the production thereof and with the use thereof.

It is known to determine antibodies and antigens by heterogenic immunological analyses (immuno assays), whereby, in principle, the following two methods are used:

For the determination of specific antibodies and especially for the determination of antiallergens, an antigen specific for the antibody to be determined is fixed on to a water-insoluble carrier material or immune adsorbent (immobilised), the so treated reagent carrier is then brought into contact with a serum sample to be investigated for antibodies, the antibody specific for the antigen fixed to the reagent carrier thereby combining with the antigen in an immunological reaction. After washing, in a second step the carrier is brought into contact with antibodies which are specific against the antibodies or immunoglobulins to be determined; these antibodies are labelled, usually either radioactively or with an enzyme. After washing, the labelling is then determined, for example the radio-activity (so-called radio-immunological test) or the enzyme activity (so-called enzyme immunological test), for example by means of colorimetric analysis.

According to a second method, the so-called sandwich method, which is particularly used for the determination of serum globulins which function as antigens, on to a carrier material are fixed antibodies acting specifically against the antigens to be determined. This carrier is then brought into contact with the serum containing the antigen to be determined, the antigens thereby combining with the antibodies. After washing, the carrier is brought into contact with antibodies which are labelled and directed against the same antigen, and, as in the case of the first method, the labelling remaining on the carrier is determined, for example the radio-activity or the enzyme activity.

For the fixing of proteins (antibodies or antigens), as carrier materials there are used synthetic resins, for example polystyrene, vinyl polymers, polypropylene, polycarbonate, silicones, rubber or treated glass (cf., for example, E. T. Maggio, "Enzyme Immuno Assay", pub. CAC Press, Florida, U.S.A., 1980, especially pages 175-178) or polysaccharides, for example cellulose (cf., for example, European Patent Specification No. 0,063,064; Bioengineering, 16, 997-1003/1974; C. J. Sanderson and D. V. Wilson, Immunology, 20, 1061-1065/1971).

A disadvantage of fixing proteins on to synthetic resin surfaces is that the antibodies are not sufficiently firmly adsorptively bound to the carrier surface so that in the case of washing and in the case of incubation, large amounts of antibodies are again desorbed, which results in a reduction of the precision and of the sensitivity. A further disadvantage is also the limited adsorption capacity of synthetic resin surfaces (cf., for example E. T. Maggio, loc. cit., p. 175). In order to achieve a better fixing of the antibodies by means of a covalent bond, attempts have also been made to activate the synthetic resin surface. Thus, for example, it is known to pre-treat polypropylene tubes with glutaraldehyde (cf., for example, S. Avrameas et al., "Immuno Enzymatic Techniques", pub. Elsevier Science Publishers, p. 163, G. H. Parsons jr., in "Methods in Enzymology", Vol. 73, Immunochemical Techniques, Part B, pub. Academic Press, 1981, pp. 224-239, especially p. 234).

A process for fixing proteins on to polysaccharide carriers is known, for example, from European Patent Specification No. 0,063,064. According to this, the polysaccharides, for example cellulose or cellulose derivatives, are activated by oxidation with sodium periodate and, after coupling with the antigen or antibody, the reagent carrier is reduced with sodium borohydride, the coupling time being said to be 8 to 15 hours. According to other methods, polysaccharides, such as cellulose or "Sephadex" particles, are activated by treatment with cyanogen bromide (cf. for example L. Wide, in "Methods of Enzymology", 73, loc. cit., pp. 203-224).

A disadvantage of these processes is the low loading density of the carrier and the long coupling times. In the case of synthetic resin carriers, there is also to be added the desorption taking place in the incubation step during the immunological determination, as well as the difficulty of producing the fleece (flat, cuttable reagent carriers); in the case of polysaccharides, there is also the laboriousness of the process (additional treatment with cyanogen bromide or periodate, whereby the periodate treatment also makes necessary a further reduction step), the dangerousness of cyanogen bromide and the formation of non-specific bindings, due to which the blank value is increased and the measurement result is falsified. Furthermore, the covalent bond formed is not stable and results in a partial dissolving off of the protein, a reduction of the sensitivity thereby being observed.

A further method of fixing for a sandwich-like immunosorbent is the formation of a precipitate (immune precipitate; cf., for example PCT-WO No. 82/02601 and U.S. patent specification No. 3,888,629). However, these methods of fixing also have the disadvantage that an additional anti-antibody is needed or an individual reagent carrier must be optimised for each test.

Therefore, it is an object of the present invention to provide a reagent paper for immunological analysis which does not possess the above-mentioned disadvantages and a process for the production thereof by means of which, in a simple, quick, economic and continuous manner, even on a large scale, reagents for the immunological analysis can be bound without precipitate formation and with homogeneous distribution, high binding capacity, low non-specific adsorption and high stability. A further object of the present invention is the provision of a reagent paper of the stated kind with increased binding capacity but without an increase of the non-specific adsorption.

Thus, according to the present invention, there is provided a process for the preparation of a reagent paper for immunological analysis, wherein a fibre fleece of a cellulose/synthetic fibre mixture, in which the weight ratio of cellulose/synthetic fibre is 1 to 90/99 to 10, is activated by treatment with periodate, the so activated fibre fleece is loaded with an acid-treated protein and non-bound protein is removed.

Furthermore, the present invention provides a reagent paper for immunological analysis, wherein it comprises a fibre fleece of a cellulose/synthetic fibre mixture, in which the weight ratio of cellulose/fibre is from 1 to 90/99 to 10.

The present invention is also concerned with the use of this fibre fleece of cellulose/synthetic fibre mixture, wherein the weight ratio of cellulose/synthetic fibre is 90 to 1/10 to 99, as a reagent carrier for the heterogeneous immunological analysis.

Thus, we have found that even the admixture of small amounts of cellulose fibres to synthetic fibres or of synthetic fibres to cellulose fibres suffices in order to achieve an improvement of the reagent carrier with regard to its use in immunological analysis. A distinct improvement was obtained when 1% or more of cellulose fibres or 10% or more synthetic fibres were admixed. The particular optimum is, in particular, dependent upon the reagents used for the analysis, the nature of the fibres and the test process. The optimum can be determined by a few preliminary experiments (for example, measurement of the binding capacity for antibodies and measurement of the nonspecific binding to the fleece).

The weight ratio of cellulose/synthetic resin fibres is preferably 10 to 80/20 to 90 and especially 20 to 40/60 to 80.

As cellulose components there can be used any cellulose fibres, for example, cellulose in the form of cotton fibres, fibres of bleached sulphite cellulose or sulphate cellulose or cotton linters. Two or more such fibres can also be used in admixture.

Synthetic fibres are preferably fibres of polyamide, regenerated cellulose or glass fibres and especially polyester fibres. Further appropriate synthetic fibres include, for example, polyacrylonitrile, polyethylene and polypropylene fibres. Here, too, mixtures of two or more synthetic fibres can be used. For the fleece structure, an addition of binding fibres can be preferable, for example the addition of polyvinyl alcohol, polyurethane, polystyrene and/or polyvinyl chloride fibres, preferably in an amount of from 0.1 to 30% by weight, referred to the amount of cellulose fibres. The fleece structure can also be improved by the addition of wet-strength agents, such as ureaformaldehydes, melamine-formaldehydes or polyamideepichlorohydrins, in an amount of from 0.1 to 30% by weight, referred to the amount of cellulose fibres. Thus, for example, there can be used "Etadurin" (manufactured by Akzo Chemie), a polyamideamine epichlorohydrin resin. An especially preferred fleece composition is, for example, one of polyester and cellulose in a ratio of from 6:4 to 8:2 and especially of 80% by weight of polyester and 201% by weight of sulphite cellulose. The properties of the fibres used for the fibre fleece correspond, as a rule, to the properties usual for such fibres, for example fibre length, fibre thickness and purity.

According to the present invention, fibre fleeces are preferably used which have been produced by the process according to the present invention.

The periodate treatment can take place under the conditions known from the prior art for such a treatment for fixing proteins to cellulose carriers. It is thereby possible to treat the fibres and especially only the cellulose fibres, prior to the formation of the fibre fleece, with periodate, for example a 1% fibre suspnsion in aqueous sodium periodate solution. Preferably, however, a treatment of the finished fibre fleece (paper) takes place, in which case, as a rule, a better homogeneity of the finished reagent paper is achieved. The activation of the fleece material can preferably take place, for example, in a beam dyeing apparatus, whereby 10 to 50 m² sized fleece surfaces can be oxidised in one batch. As oxidation medium, there is preferably used a 5 to 15 and especially a 10 millimolar aqueous solution of sodium periodate, the amount of periodate thereby preferably being 1 to 5 mMole and especially about 2.5 mMole/g. of fleece. The oxidation treatment time can be from 1 to several hours and preferably about 2 hours. After oxidation, the fleece material is washed free of periodate, which can take place, for example, in the beam dyeing apparatus, followed by drying.

The production of the fibre fleece (paper) can take place in the usual manner for the production of fleece, for example by application of a fibre material suspension of cellulose pulp and synthetic fibres in high dilution on to a paper machine sieve, sucking off and subsequent drying. The fleece (paper) advantageously has a weight per unit surface area of from 100 to 250 g./m² and has a great open porosity. The thickness is preferably from 0.1 to 1.5 mm. and especially from 0.7 to 1.0 mm.

The loading of the optionally periodate-treated, oxidised fleece material with the optionally acid pretreated protein can take place by impregnation of the fleece with a solution of the protein, for example in an impregnation plant normally used for such purposes. The impregnated fleece material is then dried, possibly washed in an after-treatment for the removal of unbound protein, for example with an aqueous buffer solution (pH 6 to 8) and subsequently dried.

The change of the physico-chemical properties of antibodies by variation of the pH value, ionic strength and temperature is known. Thus, for example, Vandenbrand et al. (Molecular Immunology, 18 (7), 621–631/1982) describe an increase of the hydrophobic properties (which manifest themselves in an increased exchange reaction with lipid model membranes) when the antibodies are first dialysed against a buffer with a pH of 2 and then against a buffer with a pH of 7. J. J. Gonvers et al. (BBA, 251, 262–273/1971) describe that rabbit IgG, after incubation at pH <4.0, forms oligomers/dimers. L. W. Hoyer et al. (Immunochemistry, 5, 277–292/1968) describe that in the case of the antibody desorption from immune adsorbers in a pH range of from 5 to 7, the addition of salt promotes the elution, whereas in a pH range of from 1 to 3, the elution is reduced by the addition of salt. From this is to be concluded that hydrophobic exchange reactions take place at low pH values. From published Japanese Patent Specification No. 57-74663, as well as from E. Ishikawa et al. (Journal of Immunoassay, 1 (3), 385–398/1980), it is known to use an acid pre-treatment of IgG for the improvement of the antibody binding to polystyrene tubes or pearls. The IgG solution is thereby "diluted" with an acidic, high molar solution and, after a short time, again "buffered up" with a second also highly molar solution. Furthermore, according to this process, working is carried out with great ionic strengths. A disadvantage of this process is that a part of the antibodies is irreversibly precipitated and this is no longer available for binding to the surface.

According to the present invention, the acidic pre-treatment of the proteins (in which case, because of the intended purpose of use for immunological analysis, the proteins are preferably antibodies) can take place in situ, i.e. during the application (loading) on to the fibre fleece, for example by impregnation of the fleece with an acidic aqueous solution of the protein; during this step, the protein is pre-treated in the acidic solution. The acidic solution of the protein is preferably a solution of the protein in an appropriate aqueous buffer solution with a weakly acidic pH value and preferably with a pH value of from 3.0 to 6.0.

However, a separate pre-treatment of the protein before application to the fibre fleece is preferred. As antibodies there are thereby preferably used DE-antibodies (DE fractions) which can be obtained after passage over DEAE-cellulose. The acid pre-treatment of the proteins can take place in any appropriate manner such as is known, for example, from the prior art. For the separate pre-treatment, the following two processes have proved to be especially preferable:

1. The DE antibody is dialysed several times against a dilute acid solution and the antibody solution is then subsequently lyophilised. The loading of the fibre fleece then takes place with an aqueous solution of the lyophilisate obtained with a pH value of from 6 to 7. As acid, there can be used, for example, lactic acid, hydrochloric acid, propionic acid, acetic acid or tartaric acid in an appropriate concentration. According to a preferred embodiment, the concentration for hydrochloric acid is, for example, 1 to 50 mM and especially 2 to 10 mM and for the above-mentioned organic acids is 1 to 100 mM and especially 5 to 30mM. The antibody (DE fraction) is dialysed against the dilute acid solution for, for example, 5 hours to 5 days, a dialysis time of from 12 to 15 hours being preferred. After the dialysis, the protein is lyophilised for storage purposes. For loading the fleece with the antibody, the lyophilisate is taken up with a buffer solution.

2. The DE antibody (preferably as lyophilisate) is taken up in dilute acid solution with a pH value of from 2 to 4 and this solution is used for the loading. Acids which can be used include, for example, maleic acid, phosphoric acid and especially lactic acid. For the preparation of the solution, in principle there can be used all buffer solutions with an appropriate pH value.

A fleece with a thickness of 1.5 mm. of 80% by weight polyester and 20% by weight sulphite cellulose binds, according to the process 1, about 40 $\mu$g. antibody/fleece with a size of 6 mm.$\times$6 mm. (which corresponds to 2.5 mg. of antibody/g. of fibre material); the binding according to process 2 is of the same order of magnitude. A matrix loaded with antibodies according to process 1 can possibly be subjected to a subsequent acid treatment; as a rule, the matrix is, however, not substantially improved in its function in this way.

With the process according to the present invention, in comparison with the prior art, substantial advantages, which could not have been foreseen, can be achieved, namely, not only with regard to the carrying out of the process but also with regard to the reagent papers obtained and the immunological analyses to be carried out therewith. Such advantages are, in particular:

The process is very well suited for large batches: thus, for example, the periodate treatment with the use of a beam dyeing apparatus and the continuous impregnation with subsequent drying of the fibre fleece in a conventional impregnation plant permits large batches to be produced. These processes are especially suitable for the continuous production of planar reagent papers with a size of from 30 to 50 m$^2$ in a batch of from 10 to 50 m$^2$ in the case of the use of technical apparatus normally used in the production of paper. The narrow quality tolerances hereby necessary for the determination of analytes of low concentration can hereby be maintained without difficulty. The loading of the fibre fleece by impregnation with protein solutions also permits an exactly adjustable dosaging and the concentrating of the protein solttions in a drying step to high loading densities. According to the process of the present invention, loading densities in the microgram range/test of, for example 40 $\mu$g. antibody/test are obtained, compared with about 100 to a maximum of 1000 ng./test according to the prior art, for example 100 to 200 ng. antibody/test in the case of using a pure polyester paper.

Short coupling times, which can amount, for example, in a technical plant to not more than 10 minutes, also contribute to the economy of the process. The process can be carried out batchwise or continuously, whereby, in the case of a continuous carrying out, as a rule an even more uniform product is obtained. Because of the simple process (for example the periodate oxidation can be carried out without the subsequent reduction step, such as is necessary according to the prior art) and the short loading times, the process can also be carried out continuously on a technical scale, which is of considerable importance for the industrial production of reagent papers. According to the process of the present invention, a good fixing of the proteins on to the carrier material is, surprisingly, also possible without additional fixing steps, which was in no way obvious: according to the prior art, the periodate treatment was always followed by a hydrogenation because it was assumed that otherwise a sufficient stability would not be achieved; according to the process of the present invention, such a subsequent hydrogenation is not necessary.

With the reagent papers according to the present invention, no desorption phenomena occur during the immunological determination and, in the case of higher binding capacity, no non-specific bindings with the labelled antibodies. Because of the high loading density, in the case of the immunological tests, in comparison with known reagent papers, substantially shorter reaction times are possible. Thus, according to the present invention, reagent papers are provided which, besides a high binding capacity, at the same time have a low non-specific fixing of other substances present in the test liquid. Thus, according to the present invention, it is possible to increase the binding capacity without, in the same way, increasing the fixing of non-specifically bound substances; this is surprising because normally an increase of the binding capacity also results in an increase of the non-specific adsorption.

The reagent papers according to the present invention display a high sensitivity in the case of low deviation and low blank values; because of the stable binding of the protein on to the carrier, they can be washed, for example, with detergents, an interference with plasma and other components of the sample thereby being kept to a minimum. Because of their properties, the reagent papers according to the present invention represent a homogeneous reagent for immunological analyses: for example by cutting up into an appropriate shape and size an exact measurement is possible. Because of their high stability, the reagent papers according to the present invention are also very well suited for use and sale in containers which contain all the reagents and reaction vessels necessary for the immunological determination. They can also be simply introduced into cups of microtitre plates or into test tubes and, because of their properties, are also well suited for use as test strips.

The following Examples are given for the purpose of illustrating the present invention; if nothing is stated to the contrary, the statements of percentage and amount are by weight.

EXAMPLE 1

This Example describes the purification of antibodies to the DE fraction.

Sheep-anti-mouse-Fcγ antiserum is mixed with sodium sulphate to 1.8 molar. The precipitate obtained is taken up in PBS (phosphate buffered saline) (pH 7.0) and the solution so obtained is subjected to a passage over DEAE-cellulose. Until use, the IgG-containing fraction is frozen (−20° C.).

EXAMPLE 2

This Example describes the activation and loading of a fleece marerial using a fleece material which is as homogeneous as possible, i.e. with a homogeneous fibre distribution and with a high constancy of weight per unit surface area and of thickness (weight per unit surface area $VC \leqq 5\%$, thickness $VC \leqq 5\%$ ($VC$ = variation coefficient).

The fleece consists of 9% polyester and 10% cellulose fibres with 1% etadurin (referred to the amount of cellulose fibres) as wet strength agent.

(a) Activation.

The activation of the fleece material took place in a beam dyeing apparatus. As oxidation agent, there was used a 10 mMolar sodium periodate solution, the amount of periodate solution being 2 mM/g. of fleece and the oxidation time being 2 hours. After this treatment, the fleece material was washed free of periodate in the beam dyeing apparatus and dried in a suspension drier. The residual moisture content was $\leqq 5\%$.

(b) Loading with protein (antibody).

The fleece material treated according to (a) was impregnated with a protein solution in a conventional impregnation plant. The composition of the protein solution was as follows: 1 to 20 mg. antibody (sheep-anti-mouse-Fcγ); pH value of the solution 3.0 to 6.0. Transport speed in the impregnation plant was 0.1 m./min. The impregnated fleece material was then dried on-line on the impregnation plant by means of a suspension drier. The residual moisture content was $\leqq 5\%$.

(c) Post-treatment.

The fleece loaded according to (b) was washed in a dyeing beam with buffer solutions (pH 6 to 8) in order to remove non-bound protein. Subsequently, the fleece was dried on a conventional impregnation plant by means of a suspension drier. The residual moisture content was $\leqq 5\%$.

EXAMPLE 3

This Example describes the use of a reagent paper according to the present invention as immune adsorber for the determination of isoamylase.

The antibody fleece according to the present invention, for example as described in the preceding Examples, was impregnated with a monoclonal antibody (mouse) (cf. Federal Republic of Germany Patent Specification No. 33 42 736) against h-salivary amylase (c~50 µg./ml.; specific liquid take-up of the fleece abot 700 ml./m²) and subsequently dried in the manner described in Example 2.

Small pieces were cut or stamped out from the so loaded fleece. For the removal of about 1000 U/l. salivary amylase from 500 µl h-serum, there was needed about 1 cm² of paper. The serum was shaken for about 30 minutes at ambient temperature with the immunosorbent paper. The residual activity of h-salivary amylase in the so treated serum was 1 to 5% and the residual activity of the h-pancreatic amylase was greater than 90%.

EXAMPLE 4

Determination of thyreotropin (TSH).

Three antibodies (receptors) were used. Receptors 1 and 3 originated from the same species (mouse) and were directed against TSH. Receptor 3 was a labelled Fab fragment. Receptor 1 was a monoclonal antibody and the Fab fragment in receptor 3 also originated from a monoclonal antibody which as directed against a determinant of the TSH other than that against which the monoclonal antibody of receptor 1 was directed. Receptor 2 originated from sheep and was directed against the Fc part of the monoclonal mouse antibody. The development of the monoclonal antibodies tcok place according to the method of Köhler and Milstein (Eur. J. Immunol., 6, 292/1976).

Reagents:

1. Incubation buffer (IB):
100 mM sodium phosphate buffer (pH 7.4).

2. Receptor 1:
Mouse-anti-TSH antiserum (receptor 1): The ascites fluid from mice containing monoclonal anti-TSH antibodies was mixed ad 1.8 M with ammonium sulphate. The precipitate was taken up in a buffer of 15 mM sodium phosphate (pH 7.0) and 50 mM sodium chloride and the solution so obtained was subjected to a passage over DEAE-cellulose.

3. Receptor 3:
Anti-TSH antibodies (monoclonal) which recognised a different determinant than receptor 1; peroxidase-conjugate (receptor 3): mouse anti-TSH-antiserum was purified in the same way as receptor 1. The subsequent obtaining of Fab from the complete antibody molecule took place according to the method of R. R. Porter (Biochem. J., 73, 119/1959). Coupling with horseradish peroxidase took place according to the method of Nakane (M. B. Wilson and P. K. Nakane, "Recent developments in the periodate method of conjugating horse radish peroxidase to antibodies", 1978, pub. Elsevier, North Holland and Biomedical Press, pp. 215-224, in "Immunofluorescence and relating staining techniques").

4. Receptor 2.
Fixing of sheep anti-mouse-Fcγ antibody (receptor 2 adsorber): sheep anti-mouse-Fcγ antiserum was mixed ad 1.8 M with ammonium sulphate. The precipitate was taken up in a buffer of 15 mM sodium phosphate (pH 7.0) and 50 mM sodium chloride and the solution thus obtained was subjected to a passage over DEAE-cellulose. The IgG-containing fraction (receptor 2) was further treated as in Example 2.

5. Indicator reagent.
1.8 mM 2,2'-azino-di-(3-ethylbenzthiazoline-6-sulphonate) (ABTS) and 3.3 mM sodium perborate in 100 mM phosphate-citrate buffer (pH 4.4).

Carrying out:

(a) Double antibody sandwich:
50 ng. receptor 1 and 170 mU receptor 3 were dissolved together in incubation buffer and applied dropwise on to a commercially available cellulose fleece with a size of 6 mm.×6 mm. and a thickness of 1.0 mm.

and then dried at ambient temperature. This reagent-containing paper fleece was called reagent carrier 1.

On to reagent carrier 1 were pipetted 40 μl of the sample to be determined or a standard solution containing a known amount of antigen, the fleece was subsequently immediately centrifuged off in an Eppendorf centrifuge, reagent carrier 1 being placed on an Eppendorf cap, the eluted liquid meeting, during the centrifuging, the receptor 2 and reacting therewith. As receptor 2, a fleece according to the present invention was used which was made of a paper mixture of 80% polyester and 20% fleece with a size of 6×6 mm. and a thickness of 0.7 mm. per test.

On a shaking apparatus, the reaction mixture was incubated for 15 minutes at 37° C., subsequently washed three times with 1 ml. amounts of IB and then 200 μl. of indicator reagent were added thereto. With two different TSH samples, the following extinctions were determined:

| TSH (μU/ml.) | $E_{405\ nm}$/cm+ |
|---|---|
| 0 | 0.74 |
| 50 | 7.54 |

+The extinction values were determined with a layer thickness of 0.2 cm. and recalculated to a layer thickness of 1 cm.

(b) Sandwichassay

The carrying out took place with the same reagents and in the same manner as described in (a) but with the following changes:

1.1 Fleece (80% polyester and 20% cellulose) containing receptor 2 was preincubated for 1 hour with 20 μg. of receptor 1 in 0.2 ml. Subsequently, the preincubated supernatant was sucked off and the fleece washed three times with, in each case, 1 ml. IB.

2. Adsorber receptor 2, pre-treated in this manner with receptor 2, was incubated for 4 hours with sample and receptor 3 on a shaking apparatus at 37° C. In this variant, the addition of soluble receptor 1 was omitted.

Subsequently, the supernatant was sucked off in the usual manner, the fleece (receptor 2) was washed and the fixed enzyme activity detected with 200 μl. of indicator reagent. The following extinction values were determined with two different TSH samples:

| TSH (μU/ml.) | $E_{405\ nm}$/cm+ |
|---|---|
| 0 | 0.20 |
| 50 | 2.87 |

+The extinction values were determined at a layer thickness of 0.2 cm. and recalculated to a layer thickness of 1 cm.

EXAMPLE 5 (COMPARISON)

The test performance was compared in dependence upon the paper formulation, namely, a reagent paper produced according to the present invention (paper 3) with a paper of 100% cellulose (paper 1) and with a paper of 100% polyester (paper 2).

All three reagent papers were compared in an enzyme immunoassay for the determination of CEA. The process for coupling of antibodies (sheep anti-mouse-Fcγ)was, in all three cases, identical; 5 mg. of antibody per g. of fibre material were used. The protein loading and the other process measures took place in the manner described in Example 2.

Working was according to the sandwich principle analogously to Example 4. As a variation of the statements in that Example, monoclonal antibodies directed against CEA were used. In the following Table, there are given the data for the non-specific binding (blank) and for the dynamic measurement range (by this is to be understood the difference between the signal for the highest standard and the zero standard) for the three reagent papers:

| paper | blank value | dynamic measurement range | lower limit of detection |
|---|---|---|---|
| 1 | 2000 mE | 1000 mE | 30 ng./ml. |
| 2 | 100 mE | 300 mE | 5 n.g./ml. |
| 3 | 600 mE | 5800 mE | 1.55 ng./ml. |

The extinctions were measured at $\lambda = 578$ nm with the use of a 3 mm. cuvette and recalculated to a layer thickness of $d = 1$ cm.

A comparison of the values given in the above Table clearly shows that with the reagent paper produced according to the present invention (paper 3) there can be obtained substantially better results than with the reagent papers which are not according to the present invention (papers 1 and 2).

EXAMPLE 6

This Example describes the loading of a fleece material with antibodies without periodate activation, there being used a fleece material which is as homogeneous as possible, i.e. with a homogeneous fibre distribution and with a high weight per unit surface area and thickness constancy (weight per unit surface area VC $\leq 5\%$, thickness VC$\leq 5\%$). The formulation of this fleece consists, according to the present invention, of 80% polyester and 20% cellulose fibres with 8% etadurin, referred to the amount of cellulose fibres, as wet strength agent.

6(a) Production of the antibody fleece.

Fixing of sheep anti-mouse-Fcγ antibodies (receptor 2).

Sheep anti-mouse-Fcγ antiserum was mixed ad 1.8 M with ammonium sulphate. The precipitate was taken up in a buffer of 15 mM sodium phosphate (pH 7.0) and 50 mM sodium chloride and the solution so obtained was subjected to a passage over DEAE-cellulose. The IgG-containing fraction (receptor 2 was further treated in the manner described hereinafter.

Loading with protein (antibody)

10 to 50 m² of the fleece were impregnated with a protein solution in a conventional impregnation apparatus. The composition of the protein solution was buffer salt and 1 to 20 mg. antibody (sheep anti-mouse Fcγ>); pH value of the solution 3.0 to 6.0. Speed of advance of the impregnation apparatus: >0.1 m./min. The impregnated fleece was then dried on-line on the impregnation apparatus by means of a suspension drier. The residual moisture content was $\leq 5\%$.

The reaction of protein-fleece took place in the wet stretch (about 5 to 8 m.) and the reaction time was <5 min.

After-treatment.

The fleece loaded according to (b) was washed in a dyeing beam with buffer solutions (pH 6 to 8) in order to remove non-bound protein. Subsequently, the fleece was dried on a conventional impregnation apparatus by means of a suspension drier. The residual moisture content was $\leq 5\%$.

6(b) Determination of thyreotropin (TSH).

Receptors 1 and 3 originated from the same animal species (mouse) and were directed against TSH. Receptor 3 is a labelled Fab fragment. Receptor 1 is a monoclonal antibody and the Fab fragment also originates from a monoclonal antibody which is directed against a determinant of the TSH different from the monoclonal antibody of receptor 1. Receptor 2 originates from sheep and is directed against the Fc part of the monoclonal mouse antibody.

The development of the monoclonal antibodies took place according to the method of Kohler and Milstein (Eur. J. Immunol., 6, 292/1976).

Reagents:

1. Incubation buffer (IB):
100 mM sodium phosphate buffer (pH 7.4).

2. Receptor 1:
Mouse anti-TSH antibody (receptor 1): The monoclonal anti-TSH antibody-containing ascites fluid of mice was mixed ad 1.8 M with ammonium sulphate. The precipitate was taken up in a buffer of 15 mM sodium chloride and the solution so obtained was subjected to a passage over DEAE-cellulose.

3. Receptor 3:
Mouse anti-TSH antibody (monoclonal) which recognises an antigenic determinant different from that recognised by receptor 1; peroxidase conjugate (receptor 3): mouse anti-TSH antiserum is purified in the same way as receptor 1. The subsequent obtaining of Fab from the complete antibody molecule took place according to the method of R. R. Porter (Biochem. J., 73, 119/1959). The coupling with horseradish peroxidase took place according to the method of Nakane (M. B. Wilson and P. K. Nakane, "Recent developments in the periodate method of conjugating horseradish peroxidase to antibodies", 1978, pub. Elsevier, North Holland Biomedical Press, pp. 215–224, in "Immunofluorescence and relating staining techniques").

4. Indicator reagent:
1.8 mM ABTS and 3.3 mM sodium perborate in 100 mM phosphate-citrate buffer (pH 4.4).

Carrying out.

(a) 50 ng. Receptor 1 and 170 mU receptor 3 were dissolved in incubation buffer and together applied dropwise to a commercially available cellulose fleece with a size of 6×6 mm. and thickness of 1.0 mm. and dried at ambient temperature. This reagent-containing paper fleece was called reagent carrier 1.

On to reagent carrier 1 were pipetted 40 μl. of the sample to be determined or of standard solution containing known amounts of antibodies. Subsequently, the fleece was immediately centrifuged off in an Eppendorf centrifuge, the reagent carrier 1 being placed on an Eppendorf cap and the eluted liquid in the cap meeting, during the centrifuging, with the receptor 2 and reacting therewith. Of receptor 2, there was used a fleece with a size of 6×6 mm. and a thickness of 0.7 mm. per test.

The reaction mixture was incubated for 15 minutes at 37° C. on a shaking apparatus, subsequently washed three times with 1 ml. amounts of IB and finally 200 μl. of indicator reagent were added thereto. With different TSH samples, the following extinctions were determined:

| TSH (μU/ml.) | $E_{405\,nm}$/cm+ |
|---|---|
| 0 | 0.74 |

| TSH (μU/ml.) | $E_{405\,nm}$/cm+ |
|---|---|
| 50 | 5.5 |

+The extinction values were determined at a layer thickness of 0.2 cm. and recalculated to a layer thickness of 1 cm.

We claim:

1. Process for the preparation of a reagent paper for immunological analysis, comprising preparing a fibre fleece of a cellulose/synthetic fibre mixture, in which the weight ratio of cellulose/synthetic fibre is from 1:99 to 90:10, wherein said fleece is activated by treating at least a portion thereof with periodate, loading said activated fibre fleece with an acid treated protein under conditions favoring binding thereto and removing non-bound protein.

2. Process according to claim 1, wherein the weight ratio of cellulose/synthetic fibre is from 10:90 to 80:20.

3. Process according to claim 1, wherein the weight ratio of cellulose/synthetic fibre is from 20:80 to 40:60.

4. Process according to claim 1 wherein the cellulose component is selected from the group consisting of cellulose, sulphite cellulose, sulphate cellulose and a linter.

5. Process according to claim 1 wherein the synthetic fibre material is selected from the group consisting of polyamide, polyacrylonitrile, regenerated cellulose, glass fibres, and polyester.

6. Process according to claim 1 wherein the protein is pretreated with acid in situ.

7. Process according to claim 1, wherein non-bound protein is removed by washing the loaded fleece with an aqueous buffer solution with a pH of from 6 to 8.

8. Reagent carrier prepared by the process of claim 1.

9. Process according to claim 1, wherein said activation is carried out before formation of the fleece.

10. Process according to claim 9, wherein only the cellulose is activated.

11. Process according to claim 1, wherein said mixture further comprises at least one binding fibre and weight strength agent in an amount of from 0.1 to 30% by weight referred to the weight of cellulose fibre.

12. Process according to claim 11, wherein said binding fibre is selected from the group consisting of polyvinyl alcohol polyurethane, polystyrene and polyvinyl chloride.

13. Process according to claim 11, wherein said wet strength agent is selected from the group consisting of polyamide-epichlorohydrins, urea-formaldehydes and melamine-formaldehydes.

14. Process according to claim 1, wherein said protein is an antibody.

15. Process according to claim 14, wherein said antibody is in an acid solution with a pH of from 2 to 4.

16. Process according to claim 14, wherein the antibody is dialysed against an acid solution to form an antibody containing solution, lyophilizing said solution and impregnating the fibre fleece with said antibody in an aqueous solution at a pH of from 6 to 7.

17. Process according to claim 16, wherein said acid is selected from the group consisting of lactic acid, maleic acid, hydrochloric acid, propionic acid, acetic acid and tartaric acid.

18. Reagent carrier comprising a fibre fleece of a cellulose/synthetic fibre mixture, wherein the weight ratio of cellulose/synthetic fibre in said carrier is from 1:99 to 90:10 and wherein the fibre fleece is loaded with an acid pretreated protein.

19. Reagent carrier of claim 18, wherein the weight ratio of cellulose/synthetic fibre is from 10:90 to 80:20.

20. Reagent carrier of claim 18, wherein the weight ratio of cellulose/synthetic fibre is from 20:80 to 40:60.

21. Reagent carrier of claim 18, wherein the cellulose component is selected from the group consisting of cellulose, sulphite cellulose, sulphate cellulose and a linter.

22. Reagent carrier of claim 18 wherein the synthetic fibre material is selected from the group consisting of polyamide, regenerated cellulose, polyacrylonitrile, glass fibres and polyester.

23. Reagent carrier of claim 18, wherein said fibre fleece is activated with periodate.

24. Reagent carrier of claim 18 wherein said carrier further comprises at least one binding fibre and wet strength agent in an amount of from 0.1 to 30% by weight, referred to the weight of cellulose fibre.

25. Reagent carrier of claim 24, wherein said binding fibre is selected from the group consisting of polyvinyl alcohol, polyurethane, polystryrene, and polyvinyl chloride.

26. Reagent carrier of claim 24, wherein said wet strength agent is selected from the group consisting of polyamide epichlorohydrins, urea-formaldehydes, and melamine-formaldehydes.

27. Process for carrying out heterogeneous immunological analysis comprising contacting a sample to be investigated with a reagent carrier, said reagent carrier comprising a fibre fleece of a cellulose/synthetic fibre mixture wherein the weight ratio of cellulose/synthetic fibre is from 1:99 to 90:10 under conditions favoring binding of a component of said ampls to said carrier and wherein the fibre fleece is loaded with an acid pretreated protein, and determining the presence or amount of said component bound to said carrier.

28. Process of claim 27, wherein said weight ratio is from 10:90 to 80:20.

29. Process of claims 27 or 28, wherein said protein is an antibody.

30. Process of claim 28, wherein said weight ratio is from 20:80 to 40:60.

31. Process of claim 28, wherein the cellulose component of said mixture is selected from the group consisting of cellulose, sulphite cellulose, sulphate cellulose and a linter.

32. Process of claim 28, wherein the synthetic fibre material is selected from the group consisting of polyamide, regenerated cellulose, polyacrylonitrile glass fibres and polyester.

33. Process of claim 28, wherein said reagent carrier contains a fibre fleece activated with periodate.

34. Process of claim 28, wherein said mixture further comprises at lest one binding fibre or wet strength agent, in an amount of from 0.1 to 30% by weight referred to the weight of cellulose fibres.

35. Process of claim 34, wherein said binding fibre is selected from the group consisting of polyvinyl alcohol, polyurethane, polystyrene, and polyvinyl chloride.

36. Process of claim 34, wherein said wet strength agent is selected from the group consisting of polyamide-epichlorohydrins, urea-formaldehydes, and melamine formaldehydes.

* * * * *